United States Patent [19]
Rottenberg et al.

[11] Patent Number: 6,165,215
[45] Date of Patent: Dec. 26, 2000

[54] METHOD FOR PRODUCING HEART VALVES

[75] Inventors: Dan Rottenberg, Haifa; Ehad Sondak, Mobile Post Misgav; Dudu Haimovich, Ramatishai, all of Israel

[73] Assignee: H.D.S. Systems Ltd., Upper Yoqneam, Israel

[21] Appl. No.: 09/180,072

[22] PCT Filed: Jul. 8, 1996

[86] PCT No.: PCT/IL96/00044

§ 371 Date: Oct. 29, 1998

§ 102(e) Date: Oct. 29, 1998

[87] PCT Pub. No.: WO97/41808

PCT Pub. Date: Nov. 13, 1997

[30] Foreign Application Priority Data

May 5, 1996 [IL] Israel ......................................... 118149

[51] Int. Cl.⁷ ..................................................... A61F 2/24
[52] U.S. Cl. ........................ 623/2.12; 623/2.17; 623/910
[58] Field of Search ................... 623/2.12, 922, 623/918, 909, 913, 916, 2.17

[56] References Cited

U.S. PATENT DOCUMENTS

| | | | |
|---|---|---|---|
| 3,966,401 | 6/1976 | Hancock | 623/918 |
| 4,050,893 | 9/1977 | Hancock | 623/918 |
| 4,192,020 | 3/1980 | Davis et al. | |
| 4,222,126 | 9/1980 | Boretos et al. | |
| 4,364,127 | 12/1982 | Pierce et al. | |
| 4,372,743 | 2/1983 | Lane | 623/2.12 |
| 4,629,459 | 12/1986 | Ionescu et al. | |
| 4,888,009 | 12/1989 | Lederman et al. | |
| 5,279,612 | 1/1994 | Eberhardt | 623/2.12 |
| 5,447,536 | 9/1995 | Girardot | 623/916 |
| 5,469,868 | 11/1995 | Reger | 623/2.1 |
| 5,549,666 | 8/1996 | Hata | 623/2 |
| 5,584,878 | 12/1996 | Love | 623/913 |
| 5,782,931 | 7/1998 | Yang | 623/916 |

FOREIGN PATENT DOCUMENTS

| | | |
|---|---|---|
| 0 224 153 | 6/1987 | European Pat. Off. |
| 2 255 394 | 11/1992 | United Kingdom. |

OTHER PUBLICATIONS

"The Influence of Manufacturing Methods on the Function and Performance of a Synthetic Leaflet Heart Valve" M.E. Leat et al., in Proceedings of the Institution of Mechanical Engineers, vol. 209, Part H: Journal of Engineering in Medicine, (1995) pp. 65–69.

*Primary Examiner*—Michael J. Milano
*Attorney, Agent, or Firm*—Fenster & Company Patent Attorneys, LTD.

[57] ABSTRACT

A method for producing valves for blood flow control having an outer sleeve and a plurality of flexible leaflets fixed to an inner surface of the sleeve, including: molding the valve to a first shape, in which the valve leaflets are in a closed position; holding the valve in a second desired shape, in which the valves are in an open position; and immersing the valve in a hot liquid while holding it in the second shape.

24 Claims, 3 Drawing Sheets

METHOD FOR PRODUCING HEART VALVES

RELATED APPLICATIONS

This application is the U.S. national stage application of PCT/IL96/00044, filed Jul. 8 1996.

FIELD OF THE INVENTION

The present invention relates generally to multi-leaflet one-way valves, and specifically to prosthetic valves for use in the heart and in heart-lung machines and heart-assist devices.

BACKGROUND OF THE INVENTION

Tri-leaflet one-way valves are well-known in the art and are commonly used in heartlung machines, heart-assist devices and as surgical prosthetic implants to replace the heart's natural valves. Such valves must have sufficient strength and resiliency to maintain their shapes and operate securely through a great many cycles, without substantial wear or failure. At the same time, the leaflets must be sufficiently flexible to open and close smoothly, with minimal pressure drop across the valve and without creating undue turbulence or hemolytically damaging the blood cells. Various materials have been used for this purpose, including primarily hemocompatible polyurethane of different grades, as well as silicones, Teflon™ and other polymers. Complex, time-consuming processes must generally be employed in order to produce valves having the desired properties. Exemplary prior art patents describing valves of this sort and methods of producing them include U.S. Pat. No. 4,192,020, to Davis, et al.; U.S. Pat. No. 4,222,126, to Boretos, et al.; U.S. Pat. No. 4,629,459, to Ionescu, et al.; and U.S. Pat. No. 4,888,009, to Lederman, et al., which are incorporated herein by reference.

U.K. patent application GB 2,255,394A, by Rottenberg, et al., which is assigned to the assignees of the present invention and is incorporated herein by reference, describes an integral tri-leaflet valve- sleeve structure and a method of producing the structure by injection molding. The structure includes a cylindrical outer sleeve, from which three flexible, fabric-reinforced leaflets extend radially inward, meeting in the center when in the closed position. Fluid pressure exerted on the valve from one end of the cylinder causes the valve to open and allows blood to flow through the cylinder in a desired direction. When the pressure is released, or when pressure is exerted from the opposite end of the cylinder, the valve closes and prevents back-flow of blood in a reverse direction.

SUMMARY OF THE INVENTION

It is an object of the present invention to provide tri-leaflet, one-way valves having leaflets of superior flexibility, so as to open with minimal pressure and close with reduced turbulence and minimal hemolysis.

It is a further object of the present invention to provide a method of producing such valves, and particularly a method of enhancing the flexibility of the valve leaflets.

In one aspect of the present invention, the valves are designed for use in an artificial heart machine, such as a heart-lung machine or heart-assist device.

In preferred embodiments of the present invention, a valve for use in an artificial heart machine comprises a cylindrical sleeve and three flexible leaflets integrally fixed to an inner surface of the sleeve and extending radially inward therefrom. The leaflets open when a fluid pressure is exerted thereon from an inlet end of the cylinder and close when a fluid pressure is exerted from the opposite, outlet end thereof. When there is no pressure differential between the two ends of the cylinder, however, the leaflets maintain a partially open position.

This partially open position is advantageous in that by reducing the closing force of the leaflets, it reduces damage to blood cells that may be caught between the leaflets during closing, but still prevents reverse flow through the valve.

In preferred embodiments of the present invention, the valve comprises elastomeric material, preferably a polyether polyurethane polymer.

In preferred embodiments of the present invention, the leaflets are thin and substantially flexible. Preferably the leaflets have hardness of approximately 70–80 Shore A units. This hardness value is, of course, related to the stiffness of the leaflets. Preferably the leaflets are between 0.1 and 0.3 mm thick.

In some preferred embodiments of the present invention, the leaflets have non-uniform thickness. Preferably the thickness of the leaflets tapers gradually from approximately 0.25 mm at outer edges thereof, adjacent to the sleeve, to approximately 0.1 mm at inner edges thereof, adjacent to the central axis of the cylinder.

In preferred embodiments of the present invention, the valve is produced by integrally molding the cylinder with the leaflets, and then immersing the molded valve in a bath of hot liquid, while the leaflets are held open by inserting a rigid mandril through the valve. Although immediately after molding, the leaflets have a relaxed position that is closed, immersing the valve in the bath causes the leaflets to assume the desired partially open relaxed position. (In the context of the present invention, the term "relaxed position" is taken to mean the position of the leaflets when no external forces are applied thereto.) Following immersion, internal viscoelastic forces in the leaflets are reduced, and the hardness of the leaflets is consequently reduced by up to 10%.

In preferred embodiments of the present invention, the valve is molded using a polymer injection process in a high-pressure molding machine. Preferably the molding machine exerts at least 50 tons of clamping force, and the injection pressure of the polymer material is at least 2800 atm. More preferably, the molding machine includes an accumulator and a closed-loop injection speed unit, as are known in the art, and the injection pressure is approximately 3500 atm. These elements are necessary in order to mold the leaflets to the desired, very small thickness.

Preferably a mold used to produce the valve in the molding machine includes air escape grooves adjacent to the inner edges of the leaflets being formed thereby, so as to prevent air being trapped in the mold and assure the integrity of the leaflets. Preferably the mold temperature during molding is approximately 110° C.

In preferred embodiments of the present invention, the rigid mandril comprises stainless steel or plastic material, and includes a substantially conical or cylindrical portion, which is preferably fixed to a base of the mandril. When the conical or cylindrical portion of the mandril is properly inserted into the valve cylinder, it holds the leaflets partially open at a fixed, predetermined angle.

In preferred embodiments of the present invention, the bath of hot liquid contains water, preferably at a temperature of 60° C. or greater, more preferably at a temperature of 80° C. or greater, and most preferably at a temperature of 82–84° C. Preferably the valve is immersed in the bath for approximately two minutes, and is thereafter immersed in a cold water bath for approximately two minutes, preferably at a temperature of 20–25° C.

Preferably the successive steps of immersing the valve in the hot water bath, and thereafter in the cold water bath, are each performed twice, in alternation.

Although preferred embodiments of the present invention are described with reference to valves for use in an artificial heart machine, it will be understood that other, similar valves produced in accordance with the present invention may be used in other areas of application of multi-leaflet check-valves. Such valves may be cylindrical, like those described in the above preferred embodiment, or they may have other external shapes, as appropriate to the applications for which they are designed.

There is therefore provided, in accordance with a preferred embodiment of the present invention, a one-way valve, including:

a cylindrical outer sleeve, having an inner surface and having an inlet end and an outlet end; and a plurality of flexible leaflets, fixed to the inner surface of the sleeve and extending radially inward therefrom, which leaflets assume a fully-open position when a sufficiently greater fluid pressure is applied to the inlet end of the sleeve than to the outlet end, and a closed position when a sufficiently greater fluid pressure is applied to the outlet end of the sleeve than to the inlet end, and wherein when the pressures applied to the inlet and outlet ends of the sleeve are substantially equal, the leaflets assume a partially-open position, intermediate between the closed and filly-open positions of the leaflets.

Preferably, the plurality of flexible leaflets includes three flexible leaflets.

Preferably, the sleeve and the leaflets include elastomeric material, preferably a polyurethane polymer, and most preferably a polyether polyurethane polymer. Preferably, the sleeve and the leaflets are integrally formed of the elastomeric material.

Preferably, the leaflets have a thickness substantially between 0.1 and 0.3 mm.

Preferably, the thickness of each leaflet tapers from a greater thickness in a vicinity of an outer edge thereof, adjacent to the inner surface of the sleeve, to a lesser thickness in a vicinity of an inner edges thereof, adjacent to a central axis of the sleeve. Preferably, the thickness of the leaflets tapers from approximately 0.25 mm to approximately 0.1 mm.

Preferably, the leaflets are substantially flexible, and have a hardness less than 80 Shore A.

Preferably, the valve described above is used in an artificial heart machine.

There is further provided, in accordance with a preferred embodiment of the present invention, a method for producing valves having an outer sleeve and a plurality of flexible leaflets fixed to an inner surface of the sleeve, including molding the valve to a desired shape and immersing the valve in a bath of hot liquid.

Preferably, immersing the valve in a bath of hot liquid increases the flexibility of the leaflets.

Preferably, molding the valve includes forming the leaflets in a closed position thereof, and immersing the valve includes holding the leaflets in a partially open position while immersing the valve, preferably by inserting a mandril into the valve.

Preferably, molding the valve comprises integrally molding the sleeve and the leaflets, preferably by injecting a polymer material into a mold under high pressure. Preferably the polymer is injected at a pressure greater than 2800 atm, more preferably at a pressure of approximately 3500 atm.

Preferably, immersing the valve in a bath of hot liquid includes immersing the valve in water at a temperature greater than 60° C., more preferably greater than 80° C., and most preferably substantially in the range 82–84° C. for approximately two minutes.

Preferably, the valve is afterwards immersed in cold water, preferably at a temperature substantially in the range 20–25° C.

Preferably, the valve is afterwards immersed a second time in a bath of hot liquid, and then a second time in cold water.

There is also provided, in accordance with a preferred embodiment of the present invention, a valve, including an outer sleeve and a plurality of flexible leaflets fixed to an inner surface of the sleeve, produced in accordance with the above method.

The present invention will be more fully understood from the following detailed description of the preferred embodiments thereof, taken together with the drawings in which:

DETAILED DESCRIPTION OF PREFERRED EMBODIMENTS

Figure 1:
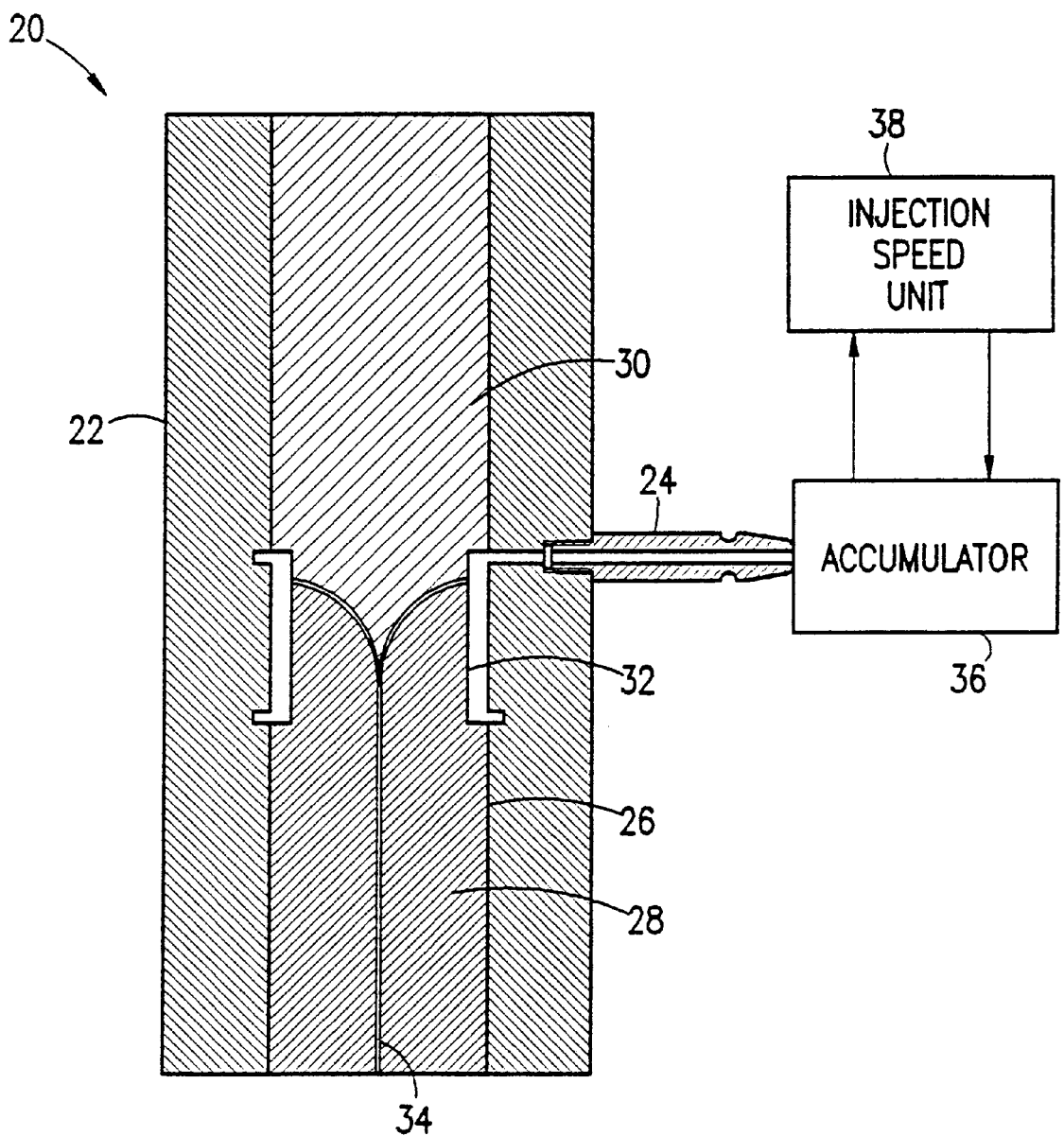
FIG. 1 is a partly schematic, sectional view of an injection press, for use in accordance with a preferred embodiment of the present invention.

Reference is now made to FIG. 1, which shows an injection molding press 20 for use in producing three-leaflet, cylindrical valves accordance with a preferred embodiment of the present invention. Press 20 comprises a housing 22 and inlet port 24, through which polymer material is injected. The press contains a mold 26, comprising female 28 and male 30 mold members.

Figure 2:
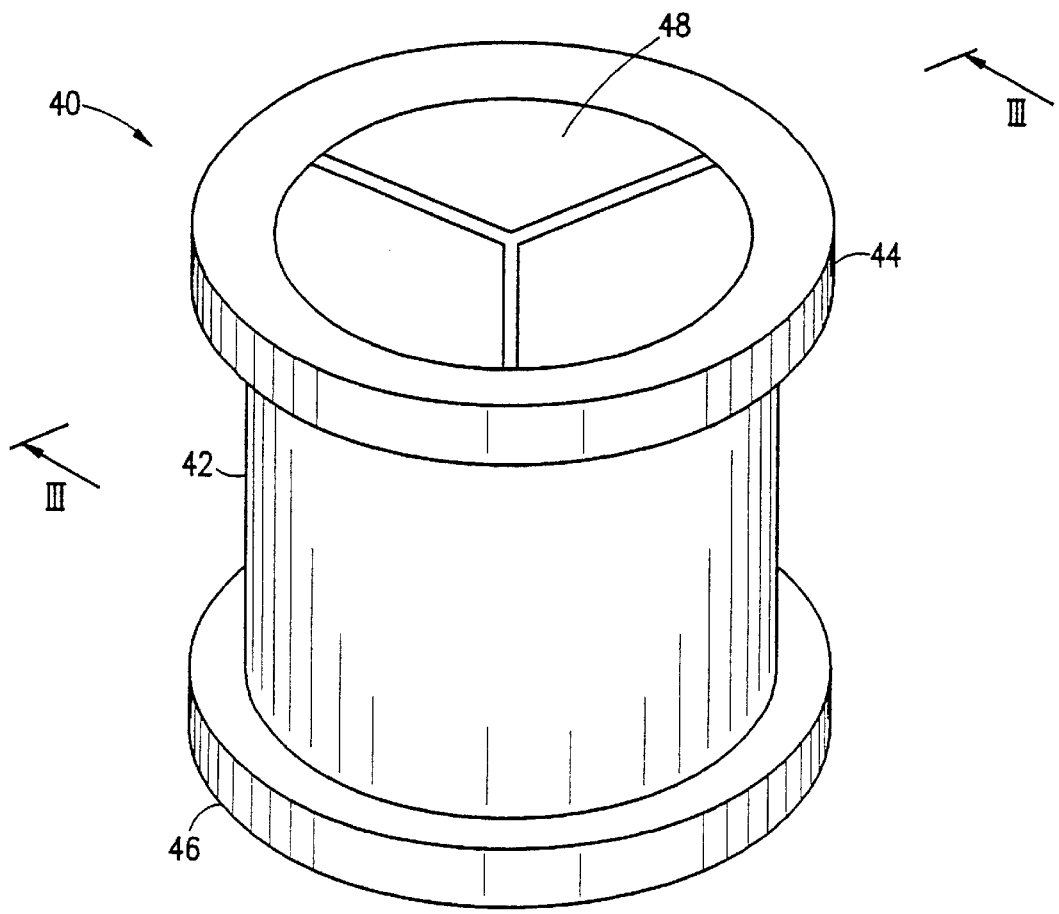
FIG. 2 is an isometric representation of a valve in accordance with a preferred embodiment of the present invention.
Figure 3:
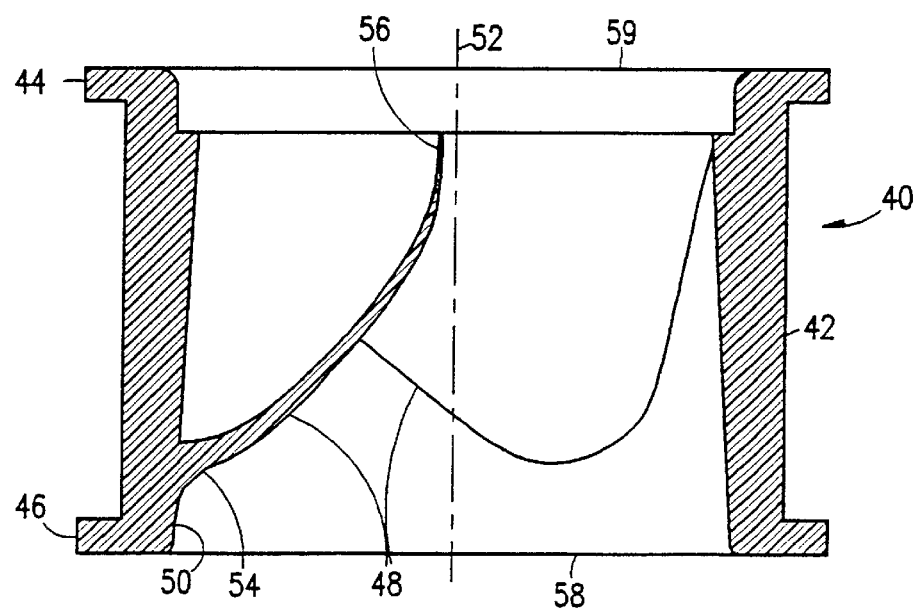
FIG. 3 is a sectional view of the valve shown in FIG. 1.

In operation, press 20 is heated to approximately 110° C., and a polymer material, preferably a hemocompatible polyether polyurethane, such as Tecoflex™ 2-80 A, manufactured by Thermedics, or Pelethane™ 2363 80A, manufactured by Dow Chemical, is injected through ports 24 and flows therethrough into space 32. Air escape grooves 34 enable air trapped in the mold, which could adversely affect the integrity of a valve thus produced, to escape. The polymer material is injected into press 20 at a pressure of at least 2800 atm, preferably about 3500 atm, using an accumulator 36 and a closed-loop injection speed unit 38, as are known in the art. The high pressure of the injection process is necessary to cause the polymer material to flow into and fill all parts of space 32, including narrow central portions thereof FIG. 2 is an isometric representation of a valve 40 produced by press 20, and FIG. 3 shows valve 40 in sectional view. Valve 40 preferably comprises an outer cylindrical sleeve 42, preferably with an upper rim 44 and a lower rim 46 protruding radially outward at either end thereof. Rims 44 and 46 are useful in securing valve 40 to a tubing assembly or other flow apparatus with which the vale operates, but they are not essential to the present invention. Three leaflets 48 are integrally fixed to an inner surface 50 of sleeve 42 and extend radially inward toward a valve central axis 52. It will be understood that FIG. 2 shows valve 40 in its fully-closed position, which is the relaxed position of leaflets 48 immediately following injection molding by press 20. In the context of the present invention, the term "relaxed position" is taken to mean the position of the leaflets when no external forces are applied thereto.

As illustrated by FIG. 3, leaflets 48 are thin compared to sleeve 42. Preferably the thickness of the leaflets tapers gradually, as shown in the figure, with thickness of approximately 0.25 mm in portions near the leaflets' outer edges 54, adjacent to sleeve inner surface 50, and approximately 0.1 mm in portions near leaflet inner edges 56.

It will be appreciated that when a differential fluid pressure is applied to valve 40, so that pressure is sufficiently greater at a lower (upstream) end 58 thereof than at an upper (downstream) end 59, leaflets 48 will open upward and outward, allowing a fluid to flow therethrough. When the pressure differential is reduced below a minimum pressure needed to open the valve or is reversed, however, leaves 48 will close and prevent fluid flow through the valve.

Figure 4A:
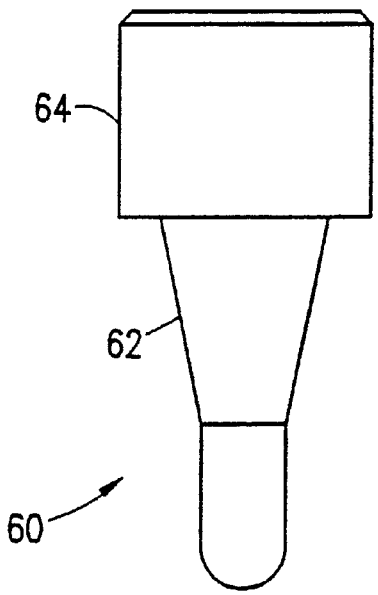
FIG. 4A is a schematic representation of a mandril, for use in accordance with a preferred embodiment of the present invention.

FIG. 4A shows a mandril 60, for use in accordance with a preferred embodiment of the present invention. Mandril 60 comprises a substantially conical portion 62, fixed to a base 64, and is preferably machined from stainless steel or rigid plastic. In place of conical portion 62, mandril 60 may similarly have a cylindrical portion or a portion of some other shape suitable for the function to be described below.

Figure 4B:
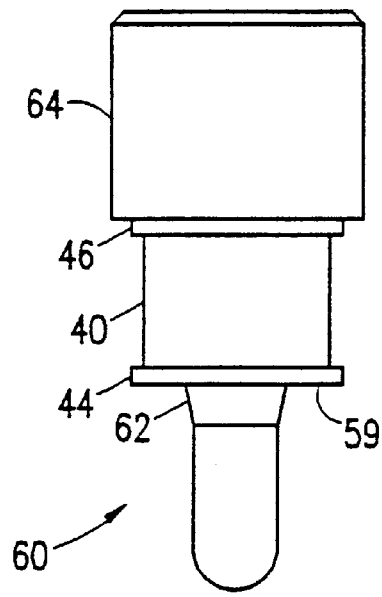
FIG. 4B is a schematic representation showing the mandril of FIG. 4A inserted into a valve in accordance with a preferred embodiment of the present invention.

As shown in FIG. 4B, after valve 40 has been molded, as described above, conical portion 62 of mandril 60 is inserted through the valve so as to hold leaflets 48 in a partially open position. The valve with the mandril inserted is immersed in a hot water bath, preferably at a temperature of 82–84° C. for a period of approximately two minutes. The valve is then placed in a cold water bath, at a temperature of approximately 20–25° C., for an additional two minutes. Preferably the valve is then re-immersed in the hot bath for another two minutes, with the mandril inserted as shown in FIG. 4B, and then placed back in the cold bath, for a final two minutes.

Figure 5:
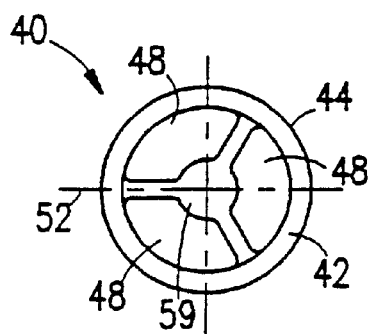
FIG. 5 is a schematic end-view of a valve in accordance with a preferred embodiment of the present invention.

FIG. 5 shows an end-view of valve 40, as it appears following the heating and cooling processes described above, so that leaflets 48 have assumed a partially-open relaxed position This partially-open position is advantageous in that it reduces damage to blood cells caught between the leaflets during closing thereof, by reducing the force of the impact exerted by the leaflets as they close. A fully-open relaxed position of the leaflets would be undesirable, however, because it would allow the leaflets to stay open at excessively low blood flow rates and could fail to prevent substantial regurgitation (i.e., reverse flow of blood) through the valve.

The hardness, and thus the stiffness, of leaflets 48 is reduced following the heating and cooling processes, due to relaxation of the viscoelastic properties of the polymer material.

Typically the hardness of the leaflets decreases by up to 10%. The low thickness and stiffness of leaflets 48 allows valve 40 to open easily, with minimal pressure drop, in response to pressure exerted on the leaflets in the appropriate direction. Similarly, the leaflets' low thickness, stiffness and natural resistance to stretch cause them to close gently when the pressure is reversed, thereby minimizing damage to blood cells.

Although the process described above results in production of a polyurethane valve having both a partially-open relaxed position and reduced leaflet stiffness, principles of the present invention may be generally applied to produce valves from other materials that have either a partially-open relaxed position, or reduced stiffness, or both these qualities.

Although preferred embodiments of the present invention are described with reference to valves for use in an artificial heart machine, it will be understood that other, similar valves produced in accordance with the present invention may be used in other areas of application of multi-leaflet check-valves. Such valves may be cylindrical, like those described in the above preferred embodiment, or they may have other external shapes, as appropriate to the applications for which they are designed. The principles of the present invention may similarly be applied to check-valves having two leaflets or four or more leaflets.

It will be appreciated that the preferred embodiments described above are cited by way of example, and the full scope of the invention is limited only by the claims.

What is claimed is:

1. A method for producing valves for blood flow control having an outer sleeve and a plurality of flexible leaflets fixed to an inner surface of the sleeve, compnrsing:

molding the valve to a first shape in which the valve leaflets are in a closed position;

holding the valve in a second desired shape, in which the valves are in an open position; and immersing the valve in a hot liquid while holding it in the second shape.

2. A method according to claim 1 wherein holding the leaflets in an open position comprises inserting a mandrill into the valve.

3. A method according to claim 1 wherein immersing the valve in a bath of hot liquid increases the flexibility of the leaflets.

4. A method according to claim 1 wherein immersing the valve in the bath of hot liquid sets the valve in the second, desired shape.

5. A method according to claim 1 wherein molding the valve comprises integrally molding the sleeve and the leaflets.

6. A method according to claim 5 wherein integrally molding the sleeve and the leaflets comprises injecting a polymer material into a mold at high pressure.

7. A method according to claim 6 wherein injecting the molding under high pressure comprises injecting the polymer at a pressure greater than 2800 atm.

8. A method according to claim 6 wherein injecting the molding under high pressure comprises injecting the polymer at a pressure greater than 3500 atm.

9. A method according to claim 1 wherein immersing the valve in a hot liquid comprises immersing the valve in hot water.

10. A method according to claim 1 wherein immersing the valve in a hot liquid comprises immersing the valve in liquid at a temperature greater than 60° C.

11. A method according to claim 1 wherein immersing the valve in a hot liquid comprises immersing the valve in liquid at a temperature greater than 80° C.

12. A method according to claim 1 wherein immersing the valve in a hot liquid comprises immersing the valve in liquid at a temperature substantially in the range of 82–84° C.

13. A method in accordance with claim 1 wherein immersing the valve comprises immersing the valve in a liquid for approximately two minutes.

14. A method according to claim 1 and comprising immersing the valve in cold liquid after said immersion in hot liquid.

15. A method according to claim 14 wherein the cold liquid is cold water.

16. A method according to claim 14 wherein the cold liquid has a temperature substantially in the range of 68–77° C.

17. A method according to claim 14 wherein said leaflet valves are held in said second. desired shape during said immersion in cold liquid.

18. A method according to claim 14 and comprising immersing the valve a second time in hot liquid followed by immersing the valve a second time in cold liquid.

19. A method according to claim 1 wherein immersing the valve in a liquid comprises immersing the valve in a bath of liquid.

20. A method for producing valves for blood flow control having an outer sleeve and a plurality of flexible leaflets fixed to an inner surface of the sleeve, comprising:

molding the valve to a first shape, by injecting a polymer material into a mold at high pressure;

holding the valve in a second desired shape; and immersing the valve in a hot liquid while holding it in the second shape, wherein molding the valve comprises integrally molding the sleeve and the leaflets.

21. A method for producing valves for blood flow control having an outer sleeve and a plurality of flexible leaflets fixed to an inner surface of the sleeve, comprising:

molding the valve to a first shape;

holding the valve in a second desired shape; and immersing the valve in hot liquid at a temperature of greater than 60° C., while holding it in the second shape.

22. A method according to claim 21 wherein the temperature is greater than 80° C.

23. A method according to claim 21 wherein the temperature is substantially in the range of 82–84° C.

24. A method for producing valves for blood flow control having an outer sleeve and a plurality of flexible leaflets fixed to an inner surface of the sleeve, comprising:

(a) molding the valve to a first shape;

(b) holding the valve in a second desired shape;

(c) immersing the valve in a hot liquid while holding it in the second shape (d) immersing the valve in a cold liquid after immersion of the valve in a hot liquid; and (e) repeating (c) and (d).

* * * * *